(12) United States Patent
Guerry

(10) Patent No.: US 11,801,212 B2
(45) Date of Patent: Oct. 31, 2023

(54) COMPOSITION AND METHOD FOR ODOR CONTROL

(71) Applicant: Thnktnk LLC (Delaware), Red Bank, NJ (US)

(72) Inventor: Raymond Guerry, Brick, NJ (US)

(73) Assignee: THNKTNK LLC (DELAWARE), Red Bank, NJ (US)

( * ) Notice: Subject to any disclaimer, the term of this patent is extended or adjusted under 35 U.S.C. 154(b) by 0 days.

(21) Appl. No.: 17/732,162

(22) Filed: Apr. 28, 2022

(65) Prior Publication Data

US 2022/0347073 A1 Nov. 3, 2022

Related U.S. Application Data

(60) Provisional application No. 63/181,088, filed on Apr. 28, 2021.

(51) Int. Cl.

| | |
|---|---|
| A61K 8/49 | (2006.01) |
| A61K 8/44 | (2006.01) |
| A61L 9/01 | (2006.01) |
| A61Q 15/00 | (2006.01) |
| A61K 8/35 | (2006.01) |
| A61L 101/36 | (2006.01) |
| A61L 9/14 | (2006.01) |
| A61L 101/40 | (2006.01) |
| A61L 101/44 | (2006.01) |

(52) U.S. Cl.
CPC .............. *A61K 8/49* (2013.01); *A61K 8/35* (2013.01); *A61K 8/44* (2013.01); *A61K 8/498* (2013.01); *A61K 8/4973* (2013.01); *A61L 9/01* (2013.01); *A61Q 15/00* (2013.01); *A61L 9/14* (2013.01); *A61L 2101/36* (2020.08); *A61L 2101/40* (2020.08); *A61L 2101/44* (2020.08)

(58) Field of Classification Search
None
See application file for complete search history.

(56) References Cited

FOREIGN PATENT DOCUMENTS

WO WO-2018094314 A1 * 5/2018 .............. A61K 8/27

OTHER PUBLICATIONS

Antiperspirants and Deodorants, Karl Laden, pp. 1-421, (pages cover, 72, 175 and 196 are attached) (Year: 1999).*

* cited by examiner

*Primary Examiner* — Kyung S Chang
(74) *Attorney, Agent, or Firm* — Barry Choobin; Patent 360

(57) ABSTRACT

A composition for reducing unpleasant odor, the composition includes betaine; musk; and N-Soya-N-ethyl morpholinium ethosulfate.

5 Claims, No Drawings

COMPOSITION AND METHOD FOR ODOR CONTROL

CROSS-REFERENCE TO RELATED APPLICATIONS

The present application claims priority from a U.S. Provisional Patent Application Ser. No. 63/181,088 filed on Apr. 28, 2021, which is incorporated herein by reference in its entirety.

FIELD OF INVENTION

The present invention relates to a composition, and more particularly, the present invention relates to a composition and method for masking odor in an enclosed environment and mitigating the body odor.

BACKGROUND

Odor or malodor refers to smells that are unpleasant to human sensory system. Odors arises from gas molecules released in the air and perceived unpleasant by the olfactory system. Odor may not cause any bodily harm, but can cause irritation, restlessness, and anxiety in humans. Odor can be masked from human sensory system by using certain aromas or fragrances, which are also molecules but perceived as pleasant by the human's sensory system. The aromas or fragrances may not inhibit the unpleasant smell but can mask it. In case of body odors, formulations, such as antimicrobials and antiperspirants can reduce body odors by killing microbes and reducing perspiration, which are the root cause of bodily odors.

A range of fragrances and anti-malodor compositions are available that vary in mode of action and type of fragrance. A desire is always there for a novel composition that has certain advantages over the known range of compositions.

SUMMARY OF THE PRESENT INVENTION

The following presents a simplified summary of one or more embodiments of the present invention to provide a basic understanding of such embodiments. This summary is not an extensive overview of all contemplated embodiments and is intended to neither identify critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a composition for reducing odor or unpleasant smell.

It is another object of the present invention that the composition is based on natural ingredients.

It is still another object of the present invention that a unique and pleasant aroma is generated.

In one aspect, disclosed is a composition comprising betaine, musk, and N-Soya-N-ethyl morpholinium ethosulfate. The disclosed composition can be used to reduce malodor in enclosed space and body odor.

DETAILED DESCRIPTION

Subject matter will now be described more fully hereinafter, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprise", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every combination of the individual steps in an unnecessary fashion.

Unless otherwise indicated, all numbers expressing quantities of ingredients used in this disclosure are to be understood as being modified in all instances by the term "about." Accordingly, unless indicated to the contrary, the numerical parameters set forth in this disclosure are approximations that may vary depending upon the desired properties sought to be obtained by the present disclosure. At the very least, and not as an attempt to limit the application of the doctrine of equivalents to the scope of any claims, each numerical parameter should be construed in light of the number of significant digits and ordinary rounding approaches.

Disclosed is a composition and method for reducing malodor in enclosed spaces/environments, such as rooms, cabins, inside of vehicles, and the like. The disclosed composition can be used topically for reducing bodily odors. The composition includes betaine, musk, and N-Soya-N-ethyl morpholinium ethosulfate. The proportions of the ingredients in the composition can be varied based on the application and can be determined experimentally. Preferably, the composition has a pH between 3.5 and 6.5. The composition can be formulated in different forms for different applications. It is understood that neutral ingredients, such as cyclodextrin can be added for making the formulation. Addition of any such neutral ingredient for formulation is within the scope of the present invention. Suitable antimicrobial agents can also be added and are within the scope of the present invention.

In one implementation, disclosed is a method of reducing odor in an enclosed space, the method includes the steps of providing a composition comprising betaine, musk, and Soya-N-ethyl morpholinium ethosulfate; and dispersing the composition in air of the enclosed space. The composition has a pH of about 3.5 to 6.5. The enclosed space can be a room or a cabin of a vehicle.

In one implementation, disclosed is a method of reducing body odor, the method includes the steps of providing a composition comprising betaine, musk, and N-Soya-N-ethyl morpholinium ethosulfate; applying the composition topically over skin.

In one implementation, the composition includes Betaine (Trimethylglycine) in an amount ranging from 0.1%-2.0%, more preferably in an amount ranging from about 0.07%-0.875%, and more preferably in an amount ranging from about 0.35%-0.7%. The composition includes N-Soya-N-ethyl morpholinium ethosulfate in an amount ranging from about 0.2%-4.0%, and more preferably in an amount ranging from about 0.13%-1.625%, and more preferably in an amount ranging from about 0.35%-0.7%. The composition includes musk in an amount ranging from about 0.05%-1.2%, and more preferably in an amount ranging from about 0.10%-0.5%, and more preferably in an amount ranging from about 0.225%-0.45%. The musk includes Ethylene brassylate, Galaxolide, Tonalide, and/or muskenone.

In one implementation, disclosed is a method for preparing the composition. The method includes the steps of mixing Betaine and N-Soya-N-ethyl morpholinium ethosulfate in a ratio of about 1:2 with 5-10% of Laureth-9 solubilizer and about 65% water. To the mix can be added Musk in a ratio of about 5:1. The composition can be added to a personal care product, laundry detergent, deodorizing spray or other products in a concentration of about 0.1-10%, more preferably about 0.2%-2.5%, and more preferably about 0.5%-2.0%.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A composition for reducing unpleasant odor, the composition comprising:
    Betaine 0.1%-2.0%;
    musk 0.05%-1.2%;
    Laureth-9 solubilizer 5%-10%; and
    N-Soya-N-ethyl morpholinium ethosulfate 0.2%-4.0%,
    wherein the composition has a pH of about 3.5 to 6.5.

2. A method of reducing odor in an enclosed space, the method comprising the steps of:
    providing a composition comprising betaine 0.1%-2.0% musk 0.05%-1.2%, Laureth-9 solubilizer 5%-10%, and N-Soya-N-ethyl morpholinium ethosulfate 0.2%-4.0%, wherein the composition has a pH of about 3.5 to 6.5; and
    dispersing the composition in air of the enclosed space.

3. The method according to claim 2, wherein the enclosed space is a room.

4. The method according to claim 2, wherein the enclosed space is a cabin of a vehicle.

5. A method of reducing body odor, the method comprising the steps of:
    providing a composition comprising betaine 0.1%-2.0% musk 0.05%-1.2%, Laureth-9 solubilizer 5%-10%, and N-Soya-N-ethyl morpholinium ethosulfate 0.2%-4.0%, wherein the composition has a pH of about 3.5 to 6.5; and
    applying the composition topically over skin.

* * * * *